(12) United States Patent
Mikeska et al.

(10) Patent No.: US 10,495,706 B2
(45) Date of Patent: Dec. 3, 2019

(54) SHIELDING OF MAGNETIC RESONANCE IMAGING APPARATUS

(71) Applicant: Elekta Limited, West Sussex (GB)

(72) Inventors: Jurgen Michael Mikeska, Dieburg (DE); Andreas Michael Hainke, Dieburg (DE)

(73) Assignee: Elekta Limited, West Sussex (GB)

( * ) Notice: Subject to any disclaimer, the term of this patent is extended or adjusted under 35 U.S.C. 154(b) by 0 days.

(21) Appl. No.: 16/182,757

(22) Filed: Nov. 7, 2018

(65) Prior Publication Data
US 2019/0137583 A1 May 9, 2019

(30) Foreign Application Priority Data
Nov. 7, 2017 (GB) .................................. 1718415.1

(51) Int. Cl.
| | | |
|---|---|---|
| *G01R 33/00* | (2006.01) | |
| *G01R 33/422* | (2006.01) | |
| *G01R 33/48* | (2006.01) | |
| *A61B 5/00* | (2006.01) | |
| *A61B 5/055* | (2006.01) | |

(Continued)

(52) U.S. Cl.
CPC .......... *G01R 33/422* (2013.01); *A61B 5/0036* (2018.08); *A61B 5/055* (2013.01); *A61N 5/1078* (2013.01); *E04B 1/92* (2013.01); *G01R 33/4808* (2013.01); *A61B 2562/182* (2013.01); *A61N 5/1049* (2013.01); *A61N 2005/1055* (2013.01); *A61N 2005/1094* (2013.01); *E04B 2001/925* (2013.01); *E04H 3/08* (2013.01)

(58) Field of Classification Search
CPC ..... G01R 33/422; G01R 33/4808; E04B 1/92; E04B 2001/925; A61B 5/055; A61B 5/0036; A61B 2562/182; E04H 3/08; A61N 2005/1055; A61N 5/1049; A61N 5/1078; A61N 2005/1094
USPC ....................................................... 250/517.1
See application file for complete search history.

(56) References Cited

U.S. PATENT DOCUMENTS

2012/0253172 A1  10/2012  Loeffler et al.
2016/0106317 A1*  4/2016  Overweg ............. G01R 33/422
                                                    600/411

FOREIGN PATENT DOCUMENTS

WO    WO2014/195158    12/2014

OTHER PUBLICATIONS

Holland Shielding, "Faraday Cage", Hollandshielding.com, Apr. 10, 2017. https://hollandshielding.com/content/Filemanager/Faraday%20cage%20 Medical%20solutions.pdf [Accessed Apr. 12, 2018].

(Continued)

*Primary Examiner* — Michael Maskell
(74) *Attorney, Agent, or Firm* — Schwegman Lundberg & Woessner, P.A.

(57) ABSTRACT

Combined MRI and radiotherapy installations require complex Faraday cage structure that encloses the room, the MRI magnets, and the patient volume, but excludes the linear accelerator path and its supply cabling. A problem with this is that the MRI magnets tend to vibrate when in use, and if physically connected to a rigid structure then the vibrations will be passed to that structure also. To alleviate this, we propose that the Faraday cage be made of a mix of prefabricated conductive sections and flexible sections of a conductive sheet. The flexible conductive sheet can be copper or aluminium, in the form of a foil or mesh.

14 Claims, 3 Drawing Sheets

(51) Int. Cl.
*A61N 5/10* (2006.01)
*E04B 1/92* (2006.01)
*E04H 3/08* (2006.01)

(56) References Cited

OTHER PUBLICATIONS

UK IPO, UK IPO Search, GB1718415.1; dated Apr. 18, 2018. 3 pages.

* cited by examiner

SHIELDING OF MAGNETIC RESONANCE IMAGING APPARATUS

This application claims priority from United Kingdom Patent Application GB1718415.1, filed Nov. 7, 2017, which is incorporated herein by reference in its entirety.

FIELD OF THE INVENTION

The present invention relates to the shielding of magnetic resonance imaging devices.

BACKGROUND ART

Magnetic Resonance Imaging ("MRI") devices operate by establishing a fixed, steady magnetic field, together with a variable gradient field, applying a radio-frequency ("rf") signal to the volume being investigated, and detecting an rf response. They therefore need to operate within a volume that is free from external rf signals. In principle, this is easily achieved by placing the device within a Faraday cage.

As the rooms provided for MRI devices were often not originally designed with this specific purpose in mind, this is usually achieved in practice by creating a custom wooden enclosure immediately within the walls of the room, which is then covered with copper sheet. This is convenient in that the wood can be trimmed to the available space using well-known carpentry techniques, and the flexible nature of the copper sheeting allows it to be tailored to the wooden construction.

This approach achieves the necessary technical standards, but is problematic in that wooden structures can be difficult to bring within fire regulations. Further, as more complex devices are introduced, such as those combining MRI and radiotherapeutic functions, the necessary shape of the Faraday cage becomes more complex and the use of a bespoke construction of this type becomes less practical.

SUMMARY OF THE INVENTION

We propose a different approach to the construction of the Faraday cage for an MRI device, especially for a combined MRI and radiotherapeutic device.

One design of such a combined device uses a linear accelerator as the radiotherapeutic source, movable on a circular path around a central horizontal axis. The MRI magnet structures are located concentrically within the circular path, around the same axis. An example is shown and described in our earlier application WO2012/076150. This requires a Faraday cage structure that encloses the room, the MRI magnets, and the patient volume, but excludes the linear accelerator path and its supply cabling. This is difficult to custom-build in wood and copper sheet.

A solution to this is to provide a prefabricated metal enclosure for the device in a part-toroidal form around the linear accelerator structure, with the MRI magnets and tunnel within the toroid. This creates one part of a Faraday cage, which can be connected in situ with a conventional part-Faraday cage around the walls of the room, with a connecting orifice between the exterior of the room and the interior of the toroid to allow for cabling (etc) to the linear accelerator structure.

A potential problem with this structure is that the MRI magnets are prone to vibrate when in use, and if they are physically connected to a rigid structure then the vibrations will be passed to that structure also. From there, the vibrations will couple to the room walls if the toroidal cage section is connected to the remainder of the cage (as it must be). This is likely to create an unpleasant environment, and may have unintended and/or undesirable resonances.

To alleviate this, we propose that the Faraday cage be made of a mix of prefabricated conductive sections and flexible sections of a conductive sheet. Prefabricated sections mean that wooden substructures are unnecessary and that an aesthetically consistent result can be obtained. However, by providing a first prefabricated section around at least part of the radiotherapeutic apparatus, a second prefabricated section around at least part of the room, and a flexible conductive sheet that connects the first and second prefabricated sections thereby to define a Faraday cage enclosing the MRI apparatus, we can ensure that the necessary rf isolation is achieved whilst also acoustically isolating the MRI and radiotherapy apparatus from the physical structure of the room.

Thus, the present invention provides a combined imaging and treatment installation, comprising a co-located radiotherapeutic apparatus and magnetic-resonance imaging apparatus, a first conductive cage, partly enclosing the radiotherapeutic apparatus, a second conductive cage, partly enclosing the magnetic-resonance imaging apparatus and the first cage, the first and second conductive cage being made up of rigid prefabricated sections, and a flexible conductive sheet that connects the first and second conductive cages, thereby to define a Faraday cage enclosing the MRI apparatus.

The radiotherapeutic apparatus and magnetic-resonance imaging apparatus are ideally co-located in that they are both located within a single room. In this case, the second conductive cage can be arranged over or define at least a part of the wall surface of the room. The flexible conductive sheet can conveniently include a portion arranged over at least a part of the floor surface and/or the ceiling of the room; these portions can be covered with tiles, which may be non-conductive if preferred. It can also include at least one portion extending across a part of a wall of the room from the ceiling to the floor, so as to provide a complete link between the two isolated cages.

The first conductive cage can be formed by a structure within the room, extending from floor to ceiling, from a first wall of the room, around the radiotherapeutic apparatus, and to a second wall of the room (which may be the same wall as the first wall). The radiotherapeutic apparatus can comprise a source that is movable along a substantially circular path around an axis, with the structure comprising a passageway disposed around the axis and within the path, and the magnetic-resonance imaging apparatus being located substantially within the passageway.

The flexible conductive sheet can be copper or aluminium, in the form of a foil or mesh. Other flexible conductive materials can be used, however, including non-metallic materials such as conductive rubber. The flexible sheet may be formed of a different material from that of the rigid sections.

BRIEF DESCRIPTION OF THE DRAWINGS

An embodiment of the present invention will now be described by way of example, with reference to the accompanying figures in which.

DETAILED DESCRIPTION OF THE EMBODIMENTS

Figure 1:
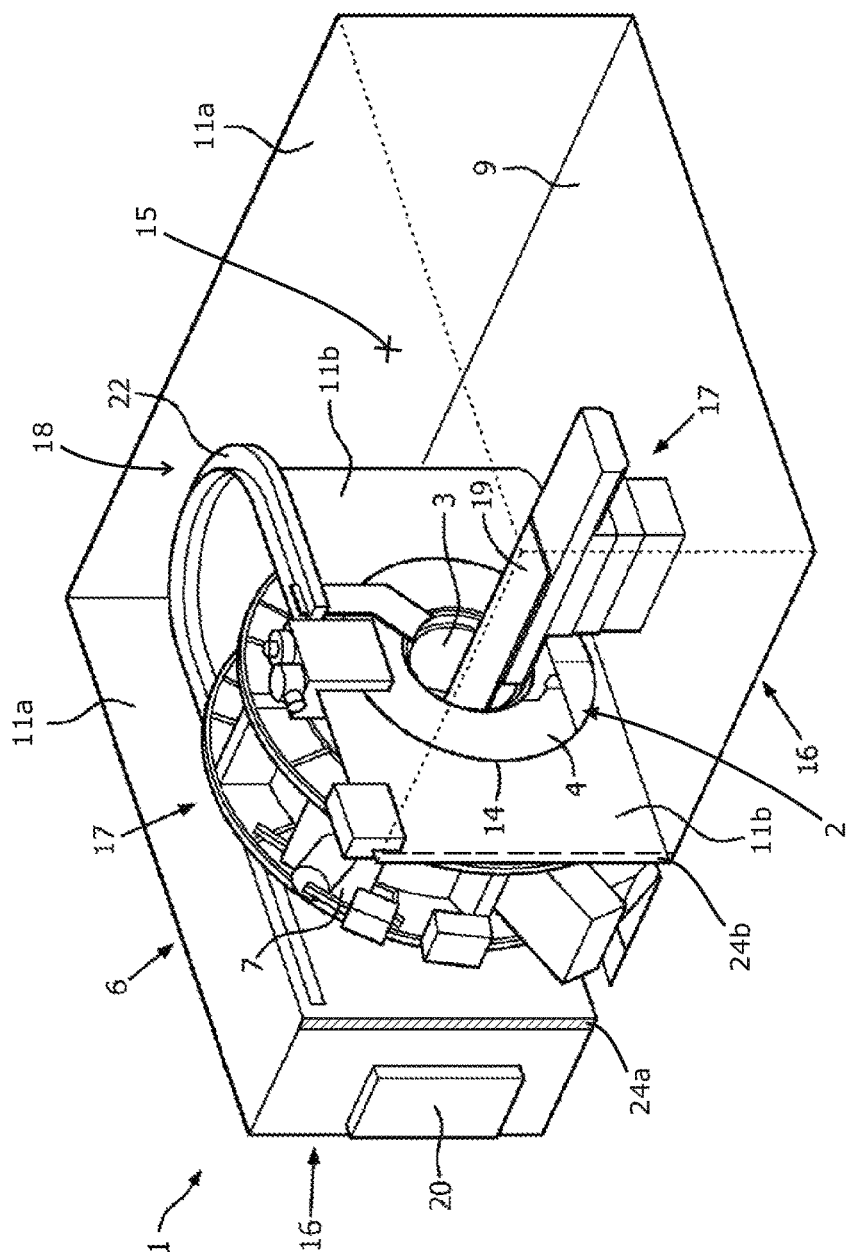
FIG. 1 shows a perspective view of an exam room of a magnetic resonance imaging system with an exam room shielding and an additional linac device according to a general setup.

FIG. 1 shows a general setup of an examination room 1 of a magnetic resonance (MR) imaging system 2. The general setup of the MR imaging system 2 comprises an examination tube 3, a main magnet 4 and a gradient coil assembly 5, whereby the main magnet 4 and the gradient coil assembly 5 are located to surround the examination tube 3, as can be best seen in FIGS. 2 and 3.

The MR imaging system 2 is part of an imaging and treatment system 6 comprising an additional radiotherapeutic device in the form of a linear accelerator and x-ray source 7, which is operated together with the MR imaging system 2. The radiotherapeutic device 7 is located at an outer circumference of the main magnet 4.

The exam room 1 has an exam room shielding generally designated as 10 for electromagnetically shielding the MR imaging system 2. Accordingly, the exam room shielding 10 is made of an electrically conductive material. The exam room shielding 10 comprises a ceiling, which is not shown in the figures, a floor 9 of the exam room 1, side walls 11 that extend from the floor 9 upwards to the ceiling. The side walls 11 of the exam room shielding 10 form the outline of a U-shaped room 15 with the longitudinal ends 13 of the examination tube 3 of the magnetic resonance imaging system 2 interconnecting the lateral flanks 16 of the U-shaped room 15. Thus, the side walls 11 are in fact made up of two groups—firstly, the room walls 11a which correspond to the (typically) four walls of the room in which the apparatus is installed apart from the area concealed by the apparatus, and secondly the side walls 11b which are the constructed walls around the MRI imaging system 2 and the radiotherapy apparatus 7. The constructed walls 11b may be integral with the apparatus 2, 7.

The constructed walls 11b are likely to acquire vibrations from the MRI system 2. To avoid passing this vibration to the room walls 11a, the shielding for the ceiling, the floor 9, and vertical strips 24a and 24b extending from the floor 9 to the ceiling at the join between the constructed walls 11b and the room walls 11a is made from a flexible conductive sheet. This can be of (for example) copper or aluminium or another conductive material. A thin sheet of up to about 0.5 mm in thickness combines both flexibility and conductivity, and is straightforward to apply. There is of course a balance to be found, as thinner sheets will be easier to form and more flexible but more susceptible to breakage, whereas thicker sheets will be more resilient but harder to form and less flexible. Likewise, woven meshes of copper and other metals are available in various weights and densities, and are suitable for use. Carbon fibre weave is widely available, and may be suitable if dense enough to provide the necessary conductivity.

Other forms for the flexible conductive sheet could include adhesive aluminium tape, which is widely available in widths sufficient to bridge a gap between rigid panels. Carbon fibre or metallic weaves could be impregnated with a flexible polymer such as a rubber-like or gel-based composition to give them greater resilience. The sheet could of course be a composite sheet made up of several elements so as to yield a sheet that is, overall, flexible and conductive.

Of course, the structure need not adopt the actual side walls of the space in which the installation is placed. If preferred, the room walls 11a can be false walls within that space. On the one hand, there is a clear incentive to take advantage of the maximum available space, but on the other hand it may be easier or more economic to construct prefabricated sections for the room walls 11a.

Where the flexible shielding is provided across the floor area of the room, it can be sandwiched between an exposed rigid floor surface (that people walk directly on), and an underlying building structure such as a concrete surface. Additional layers can also be provided above and/or below the conductive layer, for other purposes such as sound deadening or thermal insulation. In this way, the conductive layer is protected and an aesthetically pleasing surface is provided. The conductive layer can extend under the floor surface to the edges of the constructed walls 11b, where it can be attached to the conductive surfaces of the constructed walls 11b.

Equally, the flexible parts of the shielding need not cover the entire floor and ceiling. As with the vertical strips 24a, 24b, a strip may be formed in the ceiling and/or the floor which isolates the constructed walls 11b from the room walls 11a. This strip could run around the upper and/or lower extent of the constructed walls 11b, with the remainder of the ceiling and/or floor covered with or constructed of a rigid conductive layer. Alternatively, this strip could run around the upper and/or lower extent of the room walls 11a. Of course, there could be a ceiling and/or floor strip at both locations, such as a strip extending around the extremities of the ceiling and/or floor and connecting a rigid ceiling and/or floor section with the relevant wall section. Conversely, the vertical strips 24a, 24b may take up a greater part of the wall surface 11.

For reasons of aesthetics, durability and comfort, it may be preferable to conceal at least part of the ceiling and/or floor shielding with tiles suitable for ceiling and floor use. Such tiles are widely available.

The U-shaped room 15 is provided with operational spaces 17, which are located in front of the longitudinal ends 13 of the examination tube 3. The U-shaped room 15 is provided with a walkway 18 between the operational spaces 17, which is the base of the U-shaped room 15 in this embodiment. An examination table 19 is located inside the exam room shielding 10, so that a patient lying on this examination table 19, can be moved from one operational space 17 into the examination tube 3 and vice versa.

Figure 2:
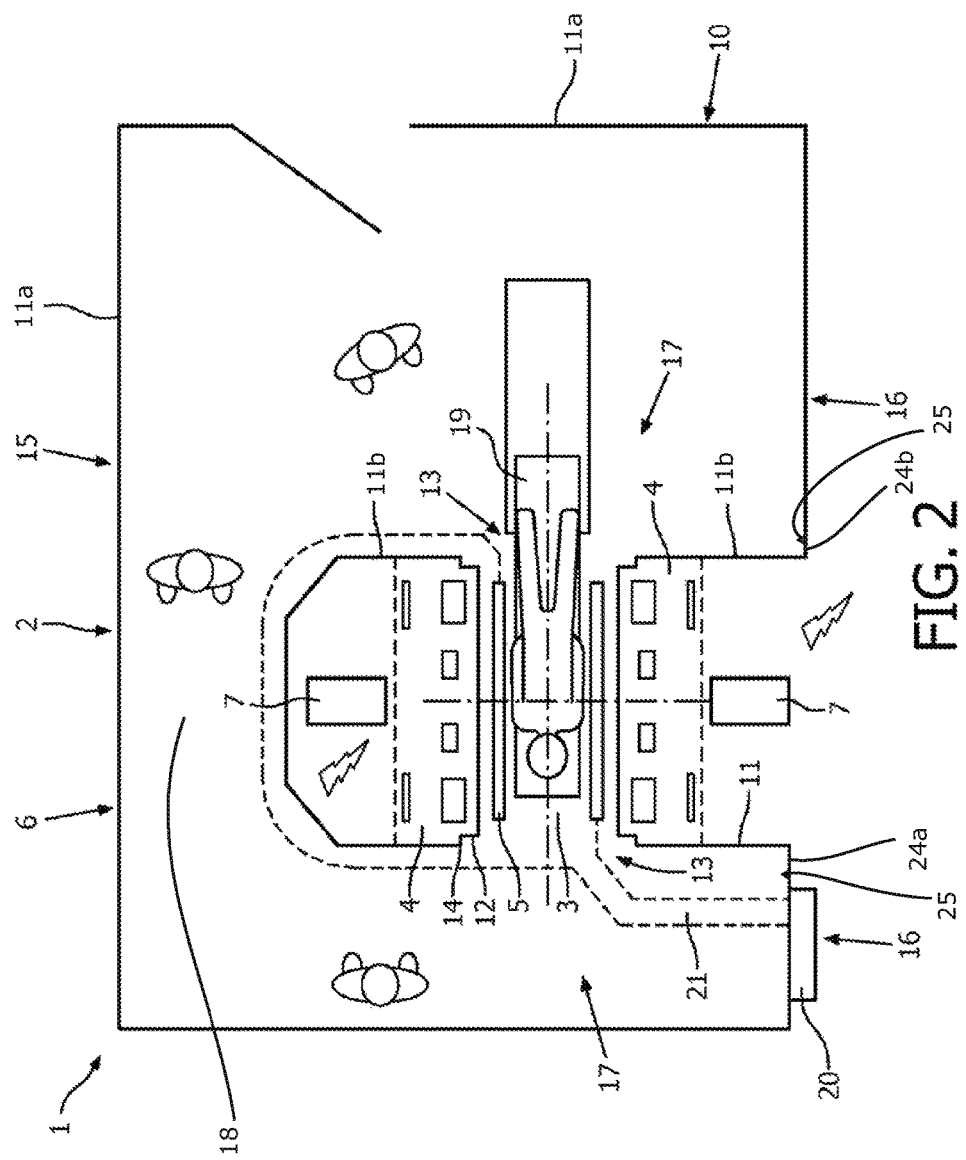
FIG. 2 schematically shows a detailed top view of the general exam room of FIG. 1 according to a first embodiment, and FIG. 3 schematically shows a detailed top view of the general exam room of FIG. 1 according to a second embodiment.
Figure 3:
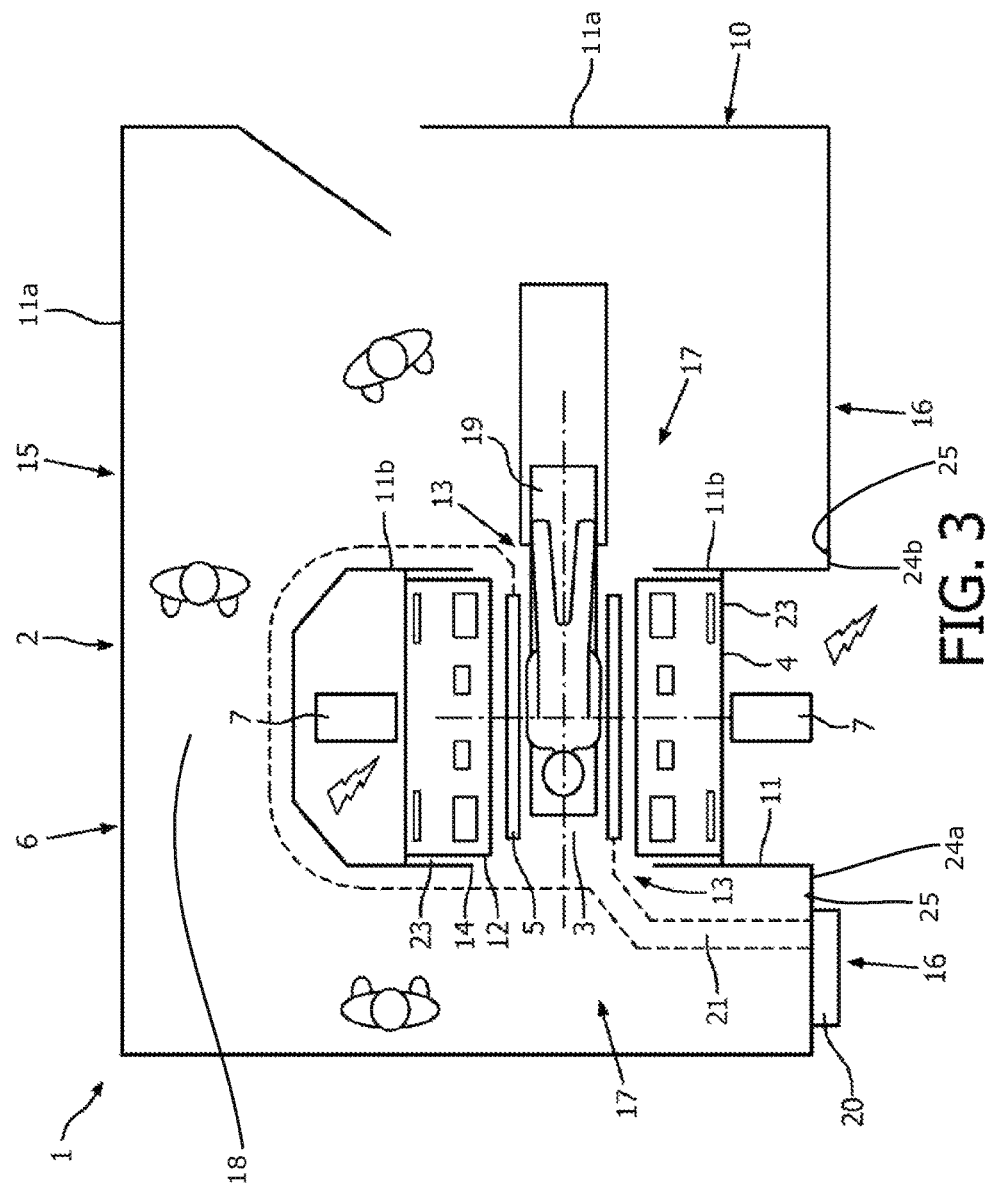

The exam room shielding 10 further comprises a filter box 20 for through connection of electrical cables 21. The electrical cables 21 are amongst others connected to the gradient coil assembly 5 at both longitudinal ends 13 of the examination tube 3, as schematically shown in FIGS. 2 and 3. As can be seen in FIG. 1, the exam room shielding 10 comprises a cable duct 22, which is arranged within an inner space of the exam room shielding 10 along a side wall 11 thereof.

Starting from this general setup, according to a first embodiment, which is shown in FIG. 2, the exam room shielding 10 further comprises a tubular shielding device 12, which is arranged to surround the examination tube 3 and the gradient coil assembly 5. The tubular shielding device 12 is made of an electrically conductive material as RF shield. The main magnet 4 and the radiotherapeutic device 7 are located at an outer circumference of the tubular shielding device 12. Both longitudinal ends 13 of the tubular shielding device 12 are circumferentially connected to openings 14 of the side walls 11 to provide an electrically conductive connection therebetween. The join between the constructed walls 11b and the room walls 11a is via the flexible sheet sections 24a and 24b. A join 25 between the flexible sections 24a, 24b and the room walls 11a is shown. Accordingly, a fully shielded compartment is formed within the exam room 1, where the examination tube 3 and the gradient coil assembly 5 as well as cables 21 are shielded from the main magnet 4 and the radiotherapeutic device 7.

Starting again from the general setup, according to a second embodiment, which is shown in FIG. 3, the exam room shielding 10 further comprises a tubular shielding device 12, which is provided integrally with the main magnet 4. The main magnet 4 is provided having an outer vacuum container 23, which is a thick-walled stainless-steel or aluminum structure and therefore conductive. As such, it can act as a suitable tubular shielding device 12. The side walls 11 of the lateral flanks 16 of the exam room shielding 10 extend over the entire circumferential flanges of the main magnet 4. The side walls 11 are electrically connected to the outer vacuum container 23 close to the outer radius of the flanges of the main magnet 4. Once again, the join between the constructed walls 11b and the room walls 11a is via the flexible sheet sections 24a and 24b, and a join 25 between the flexible sections 24a, 24b and the room walls 11a is shown. Accordingly, a fully shielded compartment is formed within the exam room 1, where the examination tube 3, the gradient coil assembly 5 and the main magnet 4 are shielded from the linac device 7, and the linac device 7 is shielded from the examination tube 3, the gradient coil assembly 5, and the main magnet 4.

It will of course be understood that many variations may be made to the above-described embodiment without departing from the scope of the present invention.

The invention claimed is:

1. A combined imaging and treatment installation, comprising:
    a co-located radiotherapeutic apparatus and magnetic-resonance imaging apparatus,
    a first conductive cage, partly enclosing the radiotherapeutic apparatus;
    a second conductive cage, partly enclosing the magnetic-resonance imaging apparatus and the first cage;
    the first and second conductive cage being made up of rigid sections;
    a flexible conductive sheet that connects the first and second conductive cages, thereby to define a Faraday cage enclosing the MRI apparatus.

2. A combined imaging and treatment installation according to claim 1 in which the radiotherapeutic apparatus and magnetic-resonance imaging apparatus are co-located within a single room.

3. A combined imaging and treatment installation according to claim 2 in which the second conductive cage is arranged over or defines at least a part of the wall surface of the room.

4. A combined imaging and treatment installation according to claim 2 in which the flexible conductive sheet includes a portion arranged over at least a part of the floor surface of the room.

5. A combined imaging and treatment installation according to claim 4 in which the portion is covered with floor tiles.

6. A combined imaging and treatment installation according to claim 5 in which the floor tiles are non-conductive.

7. A combined imaging and treatment installation according to claim 2 in which the flexible conductive sheet includes a portion arranged over at least a part of the ceiling surface of the room.

8. A combined imaging and treatment installation according to claim 7 in which the portion is covered with ceiling tiles.

9. A combined imaging and treatment installation according to claim 8 in which the ceiling tiles are non-conductive.

10. A combined imaging and treatment installation according to claim 2 in which the flexible conductive sheet includes at least one portion extending across a part of a wall of the room from the ceiling to the floor.

11. A combined imaging and treatment installation according to claim 2 in which the first conductive cage is formed by structure within the room extending from floor to ceiling, from a first wall of the room, around the radiotherapeutic apparatus, and to a second wall of the room.

12. A combined imaging and treatment installation according to claim 11 in which the first wall and the second wall are the same wall.

13. A combined imaging and treatment installation according to claim 11 in which the radiotherapeutic apparatus comprises a source that is movable along a substantially circular path around an axis, the structure comprises a passageway disposed around the axis and within the path, and the magnetic-resonance imaging apparatus is located substantially within the passageway.

14. A combined imaging and treatment installation according to claim 1 in which the flexible conductive sheet is made up of one or more of copper or aluminium foil or mesh.

* * * * *